United States Patent [19]

Alt

[11] Patent Number: 4,919,136

[45] Date of Patent: Apr. 24, 1990

[54] VENTILATION CONTROLLED RATE RESPONSIVE CARDIAC PACEMAKER

[76] Inventor: Eckhard Alt, Eichendorffstrasse 52, 8012 Ottobrunn, Fed. Rep. of Germany

[21] Appl. No.: 250,060

[22] Filed: Sep. 28, 1988

[30] Foreign Application Priority Data

Sep. 28, 1987 [DE] Fed. Rep. of Germany ....... 3732640

[51] Int. Cl.$^5$ .............................................. A61N 1/00
[52] U.S. Cl. ................................ 128/419 P; 128/734; 128/723
[58] Field of Search ............ 128/734, 419 PG, 419 D, 128/723, 635, 697, 902

[56] References Cited

U.S. PATENT DOCUMENTS

| | | | |
|---|---|---|---|
| 3,593,718 | 7/1971 | Krasner et al. | 128/419 PG |
| 4,566,456 | 1/1986 | Koning et al. | 128/419 PG |
| 4,567,892 | 2/1986 | Plicchi et al. | 128/419 PG |
| 4,576,183 | 3/1986 | Plicchi et al. | 128/419 PG |
| 4,596,251 | 6/1986 | Plicchi et al. | 128/419 PG |
| 4,694,830 | 9/1987 | Lekholm | 128/419 PG |
| 4,697,591 | 10/1987 | Lekholm et al. | 128/419 PG |
| 4,702,253 | 10/1987 | Nappholz et al. | 128/419 PG |
| 4,721,110 | 1/1988 | Lampadius | 128/419 PG |
| 4,722,342 | 2/1988 | Amundson | 128/419 PG |
| 4,730,618 | 3/1988 | Lekholm | 128/419 PG |
| 4,733,667 | 3/1988 | Olive et al. | 128/419 PG |
| 4,757,815 | 6/1988 | Strandberg et al. | 128/419 PG |
| 4,823,797 | 4/1989 | Heinze et al. | 128/419 PG |

OTHER PUBLICATIONS

"Comparative Evaluation of Two Respiratory Sensing Rate Responsive Pace-Makers," Chu-Pak Lau, et al., PACE, vol. 11, Apr. '88, p. 487.

Primary Examiner—Francis Jaworski
Assistant Examiner—George Manuel
Attorney, Agent, or Firm—Laurence R. Brown; Alfred J. Mangels

[57] ABSTRACT

The rate of pacing pulses in a rate responsive pacemaker is controlled from data representing respiration characteristics in a patient detected by intracardiac impedance measurements for more reliable control. These measurements give more reliable data for the critical pacing pulse rate control then prior art impedance measurements within the human thorax, which necessarily detect impedance changes in various tissues following respiration activity. Thus the respiration produces opposite effects on variations of impedance of pulmonary tissue and of blood, which partially cancel each other and therefore compromise the validity of transthoracic impedance based measurements of respiration. Improved respiratory activity signals reducing the unwanted effects of the pulmonary impedance changes are obtained by measuring impedance strictly within the heart. The intracardiac impedance measurements are filtered through a low pass filter to isolate the ventilation activity where amplitude is related to the tidal volume. Nonlinearities of this amplitude signal related to the physioloical activity of a patient are found to be related inversely to the respiratory rate, and are accordingly corrected to provide control signals faithfully representing the true ventilatory tidal volume. Thus, ventilation signals representing tidal volume become a reliable factor for use in pacing pulse rate control.

12 Claims, 6 Drawing Sheets

REST STANDING ON TREADMILL

PNEUMOTACHOGRAPHY
TRANSTHORACIC MEASUREMENT

INTRACARDIAC MEASUREMENT

FIG. 6.

REST  EXERCISE

PNEUMOTACHOGRAPHY

VENTILATION CONTROLLED RATE RESPONSIVE CARDIAC PACEMAKER

This invention relates to my concurrently filed co-pending application Ser. No. 07/250,155 entitled Cardiac and Pulmonary Physiological Analysis via Intracardiac Measurements with a Single Sensor, in that a pacemaker electrode implanted in a patient's heart is commonly used for measurement of cardiac and pulmonary activity and for pacing.

TECHNICAL FIELD

This invention relates to the analysis of instantaneous physiological parameters affecting the heart and more particularly it relates to means and methods of more accurately detecting and analyzing pulmonary physiological parameters of a patient with electronic measurements within the heart to derive therefrom information used for the control of a cardiac pacemaker in accordance with dynamic and historic changes incurred in physiological activity of the patient. It further provides an improved system to determine true ventilatory tidal volume as a function of the cardiovascular condition of a patient from measured amplitude data derived from an intracardiac impedance signal.

BACKGROUND ART

Pacemaker rate control is conventionally derived from control signals obtained from a plurality of measuring elements such as cardiac catheters, special breathing sensors, body temperature sensors, etc. Functional parameters used for the control of the pacing rate are dependent upon both a patient's physical condition and dynamically changing parameters. It is desirable to have the pacing rate controlled by information derived from parameters truly representing the patient's physiological condition.

Some available publications describe pacing rate control of a pacemaker by measured signals based on the detection of one physiological functional parameter to provide pacing rate control dependent upon pulmonary activity. Thus, in U.S. Pat. No. 4,567,892, G. Plicchi, et al., Feb. 4, 1986, the respiratory rate is determined from an implanted secondary electrode by an impedance measurement. In U.S. Pat. No. 4,697,591, A. Lekholm, et al., Oct. 6, 1987, the respiratory rate is determined from impedance across the chest cavity by using the can and heart implant electrodes. In U.S. Pat. No. 4,596,251, G. Plicchi, et al., June 24, 1986, the respiratory minute volume is measured by impedance changes from an additional measuring electrode located in the chest cavity. Other related respiratory rate controls are effected in U.S. Pat. Nos. 3,593,718, J. L. Krasner et al., July 20, 1971; 4,721,110 M. S. Lampadius, Jan. 26, 1988 and 4,702,253, T. A. Nappholz et al., Oct. 27, 1987. In U.S. Pat. No. 4,576,183 G. Plicchi, et al., Mar. 18, 1986 subcutaneous electrodes in a patient's chest are used to measure impedance for control by a respiratory parameter.

Recently there have also been proposals to control the pacing rate of a cardiac pacemaker from two or more physiological functional parameters. In German Patent P 36 31 155 C2, published Mar. 24, 1988, pacing rate is controlled for stable long-term control from the temperature of the venous blood within the heart and from an activity sensor for short-term exercise related activity. The temperature signals can be modulated by the activity signals for an optimal adaptation of the pacing rate to the particular exercise of the patient. Different sensors may be used to check the two functional parameters. The pacemaker control is based on the finding that essentially only absolute values such as the blood temperature and activity should be used for determining a relationship between these parameters and the pacing rate, whereas other physiological functional parameters are merely relative parameters, which at least impede stable long-term control of the pacemaker. U.S. Pat. No. 4,722,342, D. Amundson, Feb. 2, 1988 provides a plurality of different body activity sensors to derive variable pacer controls for body activity.

Respiratory control of a pacemaker pulse rate with a respiratory signal derived from analyzing the stimulation pulse reaction on the already implanted pacemaker electrode is set forth in U.S. Pat. No. 4,694,830 issued to A. Lekholm Sept. 22, 1987.

U.S. Pat. No. 4,702,253, supra, discloses a metabolic-demand pacemaker in which the standby rate is a function of respiratory minute volume. This invention is based upon the finding that ventilation effects a change in the diameter of blood vessels in the immediate vicinity of the heart. The blood in the vessels comprises a volume conductor, and its impedance is measured by establishing a known current field and measuring the voltage which develops in the field. Preferably, the voltage is measured between the high right atrium or the superior vena cava and the pacemaker case, whereby the superior vena cava is assumed to be the ideal vessel for use. The modulation in the impedance measurement is assumed to be a direct measure of minute volume. A linear relation of the degree of impedance changes in the superior vena cava to minute volume is assumed to be present. By summing the values of the degree of impedance changes, a direct measure of minute volume is assumed to be obtainable to serve for control of the pacemaker rate. It is shown hereinafter that corrections must be made for non-linearities in order to properly control the pacemaker rate.

According to the prior art, the change in thoracic impedance was determined between an implanted pulse generator can in the chest and the tip of a secondary electrode in the heart. The basis for these measurements is the empirical fact that breathing causes a change in impedance as the sum of a plurality of cumulative resistances. Each individual tissue and its corresponding share of resistance has a corresponding influence on a total impedance. Various body tissues with their individual impedances have a corresponding share of the total measured value. The greatest influence is exerted by blood, lung, fatty tissue, connective tissue and myocardium, including the transition impedances between two adjacent tissues. Both the transition impedances and the impedance of the fatty and connective tissue are largely independent of respiratory and cardiac activity. Thus, they influence the absolute value of total impedance but do not make any essential contribution to its fluctuations due to breathing and heartbeat activity. Regarding the variation of intrathoracic impedance alone, blood and lung are decisive as the main influencing variables. In accordance with the predominance of lung tissue, impedance fluctuations occur when impedance changes are determined between a pacemaker can and the tip of a secondary electrode implanted above the right hemithorax. These fluctuations are mainly due to a change in the distance between the two measuring points and to a decrease or increase of lung structure due to respiratory activity.

Comparing the various individual impedances of the human body with varying electrical conductivity, impedance resistance Z measured between two points is determined by the particular share of resistance tissue with the specific resistance R, length L and the particular cross-sectional area A. Thus $Z=RA/L$. Regarding the thorax as a volume body, $Z=RL^2/V$.

These theoretical considerations make it clear that measurements between the pacemaker can and the tip of a routinely used stimulation electrode show impedance changes due to breathing which are determined by the events of the heartbeat, blood circulation and by respiratory activity. The relatively low specific resistance of blood is the major influencing factor in impedance measurements, since it has a specific resistance of approximately 100 ohms times cm at a hematocrit of 45%, compared to the lung with approximately 1000 ohms times cm. It is clear that the total impedance only changes slightly due to breathing in spite of the predominant volume of the lung in measurements in the area between the pacemaker can and the tip of the stimulation electrode. Also, the cardiac and circulatory fluctuations behave contrary to the pulmonary impedance fluctuations and thus virtually compensate for pulmonary fluctuations. This is due to the increase of lung impedance due to inhalation, on the one hand, and to the drop of intracardiac, intravascular and hilar (vessels of the root of the lung) impedance due to inhalation within the measured path between the tip of the stimulation electrode and the pacemaker can, on the other hand.

These theoretical considerations have been proven and supported in numerous experiments. It was additionally shown that the change in volume of the superior vena cava, which clearly responds in particular to the patient's change of position, is an important determinant value for impedance. It was also shown that in measurements in which the superior vena cava is located in the measured path to the pacemaker can, the changes in volume and diameter of the superior vena cava due to speaking, and thus the changes in the resistance value of the low-impedance blood column of the superior vena cava are even predominant compared to the changes in the lung due to breathing. The concept aimed at by other investigators of determining respiratory activity by determining the thransthoracic changes of impedance between the cardiac apex and the pacemaker can, is therefore, according to our tests, very susceptible to disturbance compared to non-ventilation influences such as pressing, coughing, speaking, laughing and sudden changes of position. Furthermore, the relation is unfavorable between the information signal—breathing—and the interference signal—the above mentioned influences not due to breathing.

Previous tests for determining the transthoracic impedance fluctuations due to breathing assumed that an increase of thoracic impedance must be expected inspiratorily due to increased inspiratory lung tissue of high impedance. Our investigations showed that determination of the lung impedance changes due to breathing often leads to incidental and unstable results due to changes resulting from blood volume. Furthermore, we found that the simultaneously determined cardiac and circulatory changes of impedance in transthoracic measurement do not have any directional and reproducible valence, i.e., they are of only limited value for an implantable pacemaker system. This especially holds true if the amplitude of the ventilation of the patient is to be detected from the amplitude of those impedance measurements.

Accordingly, problems not solved by this typical prior art, must be considered and overcome, such as the detection of low level signals that may be masked in the presence of stimulation pulses, as in Lekholm, supra. Further, the presence of multiple electrodes provide probable interference and error depending upon positioning and are generally not feasible when implantation is required. For example, when considering pulmonary activity, critical to dynamic changes of a patient's physiological parameters necessary for pacing rate control, measurements in the chest will introduce significant errors in the presence of motion, coughing, sneezing, laughter, etc. which make pacing rate control from such signals responsive to undesired sensed conditions not a function of continued exercise or exertion, which are otherwised detectable from pulmonary activity. Other sensing systems, such as with body temperature, introduce time delays so that a very accurate dynamic real time control is not feasible.

Therefore, it is an object of this invention to provide more reliable determination of a patient's minute ventilation.

A further object of this invention is to provide control of pacing rates tailored to respond to individual exercise and respiratory characteristics of a patient, rather than to rely solely upon instantaneously sensed parameters.

SUMMARY OF THE INVENTION

The present invention affords a single sensor located within the right heart operable to measure the single intracardiac functional parameter, namely impedance. This sensor in the case of a patient having a pacemaker is the already implanted stimulus electrode. Accordingly, both intrathoracic pressure fluctuations correlating with the patient's breathing and the activity coming from the heart itself can be detected using only one measuring element already implanted within the heart for pacing. This invention depends upon the discovery that respiratory activity effects changes in cardiac parameters useful to produce more accurate control of pacemaker signals in responsive to dynamic activities of the patient. These changes are sensed at a single implanted detector electrode measuring a single cardiac parameter, preferably impedance.

According to the results of many investigations conducted in healthy persons and pacemaker patients by applicant, it has been determined that the impedance changes obtained according to U.S. Pat. No. 4,702,253 correlate with respiration only if certain conditions are fulfilled. Thus, the patient must not change his body position, nor move the arms, and must avoid coughing and speaking. In particular, it is found that changes in posture from supine to upright affect the volume of the blood vessels in the vicinity of the heart, especially the superior vena cava, far more than respiration does. Despite the same tidal volume, the modulation of the degree of impedance changes with respiration gives completely different results with upright position compared to supine position. This especially holds true if the amplitude of the impedance signal is considered and correlated to respiratory tidal volume. Applicant has determined that speaking, coughing and laughing also exhibits significant changes of impedance in the superior vena cava that exceed the effects of ventilation by far. This is due to the fact that the venous vessels have very thin walls and that pressure variations easily effect significant changes in diameter and volume of those vessels.

Further the impedance measurements of U.S. Pat. No. 4,702,253 are susceptible to noise because of the relatively small changes in signal amplitudes with ventilation. This is due to the fact that inspiration results in an increased amount of air in the thorax, thus producing an increase in impedance and on the other hand, an increased volume of blood in the intrathoracic vessels, thus generating a reduction of impedance. These effects partially cancel each other, and so the over-all effect varies with and is influenced by many noise variables and in general superimposed upon lower signal amplitudes.

Therefore it is an object of the present invention to provide more reliable determination of the patient's minute ventilation without compromise by changes in body position, posture, movements of the upper limbs or the chest, speaking, laughing, coughing, etc. In contrast to the thin-walled venous vessels, the considerably thicker wall of the right ventricular myocardium represents a much better protection against signals other than respiration or cardiac activity. Experimental data involving a multiplicity of healthy people and of various kinds of patients leads to the conclusion that the most reliable and noise-free manner of long term stable monitoring of ventilation is through the detection of low-frequency changes of physiological intracardiac parameters such as pressure, blood flow or volume. The preferred and most practical method of measuring changes of ventricular volume is to monitor intracardiac impedance. This produces a clear advantage over the methods described by Chu-pak Lau in Pace 11, A 24, P.487, 1988, which relate erratic rate increases in impedance controlled rate responsive prior art pacemakers of up to 145 beats/minute induced by arm swinging.

The present invention additionally determines more accurately relative changes in respiratory tidal volume dependent on the individual cardiocirculatory state. Thus, nonlinear relationships of the amplitude of impedance changes to true respiratory tidal volume are recognized and corrected to obtain more accurate measurements of the individual ventilatory capacity and the instantaneous circulatory condition of the patient.

Investigations by applicant correlate breathing and intrathoracic pressure fluctuations with the impedance measurement of blood in the heart. Thus pacing may be controlled by reliably produced physiological variations of the patient from which are derived control algorithms dependent upon such parameters as the depth of respiration and the respiratory rate. Great advantages are obtained in control of a cardiac pacemaker in response to these detected signals. Significant in the preferred sensor embodiment is the simple construction with the measuring element constituting the simultaneously used pacing stimulation electrode, thus necessitating no further implants.

Further advantages over the prior art systems is the reduction of noise in the signals. Thus, the signals are essentially only the desired physiological parameters needed for pacing rate control, and noises such as introduced by coughing or body movement and by electronic interference are significantly minimized.

An essential advantage of the invention is that the sole intracardiac measurement, preferably impedance, allows for respiratory and cardiac functional parameters to be clearly distinguished from each other. This is not possible with prior art measurements such as the impedance measurement of breathing with a thoracic secondary electrode, in part because there is an opposite effect of ventilation on impedance changes of the lungs and the vascular system, namely an increase in pulmonary impedance with inspiration, but a decrease in cardiovascular impedance. Therefore, measurements within the thorax that detect both these changes produce only very small signal levels since the opposite impedance changes cancel each other so that the overall information signal has little indicative value and is superimposed by high interference. Such mutual interference of respiratory or pulmonary and cardiac functional parameters is reliably eliminated by this invention.

BRIEF DESCRIPTION OF THE DRAWINGS

The invention shall be explained in more detail in an exemplary embodiment in connection with a cardiac pacemaker with reference to the accompanying drawings, in which:

FIGS. 2 and 3 show in block diagram form the electronic diagnosis system of a preferred embodiment afforded by this invention, FIGS. 4A and B are waveform charts showing the effects of incidental activities other than ventilation on impedance signals ($Z_H P$ representing a high pass filtered signal and $Z_{LP}$ representing a low pass filtered signal below 1 Hz) sensed at the superior vena cava (transthoracic) which are unrelated to desired physiological parameters for rate control, and which are in accordance with this invention minimized, FIG. 5A and B are waveform charts comparing high pass and low pass filtered impedance signals for transthoracic and intracardiac measurements of impedance with directly obtained ventilation signals (pneumotachography)

THE PREFERRED EMBODIMENTS OF THE INVENTION

Figure 1:
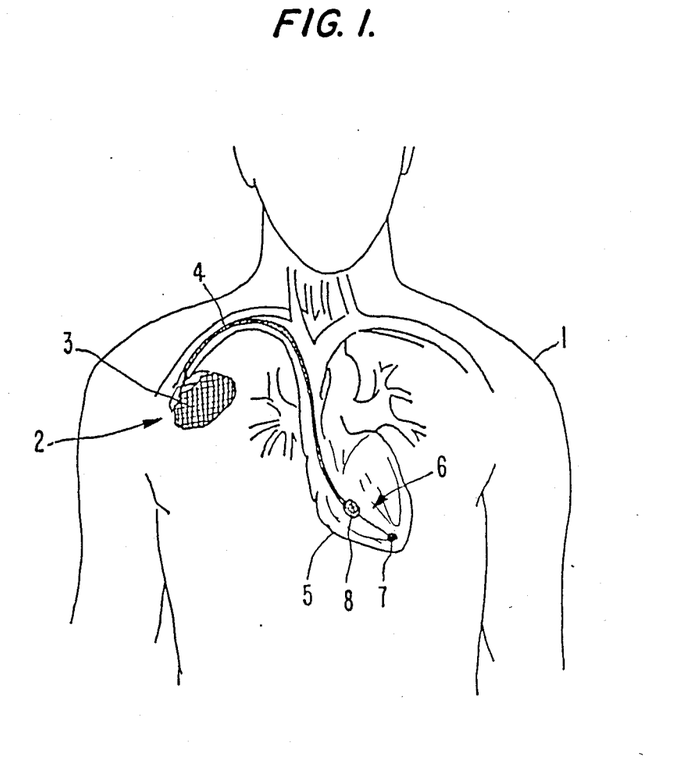
FIG. 1 shows a schematic view of an inventive cardiac pacemaker electrode system implanted in a patient's right heart.

FIG. 1 shows a cardiac pacemaker 2 implanted in a patient 1, comprising a can 3 from which a probe 4 leads via a vein into heart 5. Probe 4 is designed at its front end located in the ventricle as a sensor-pacer electrode 6 having a first pole 7 located at the tip of the probe and a second pole 8 located more proximally. As seen from FIG. 2, electrical lines 9 and 10 within probe 4 connect the two spaced poles 7 and 8 located within the right ventricle with a control circuit 11 disposed in can 3.

Figure 2:
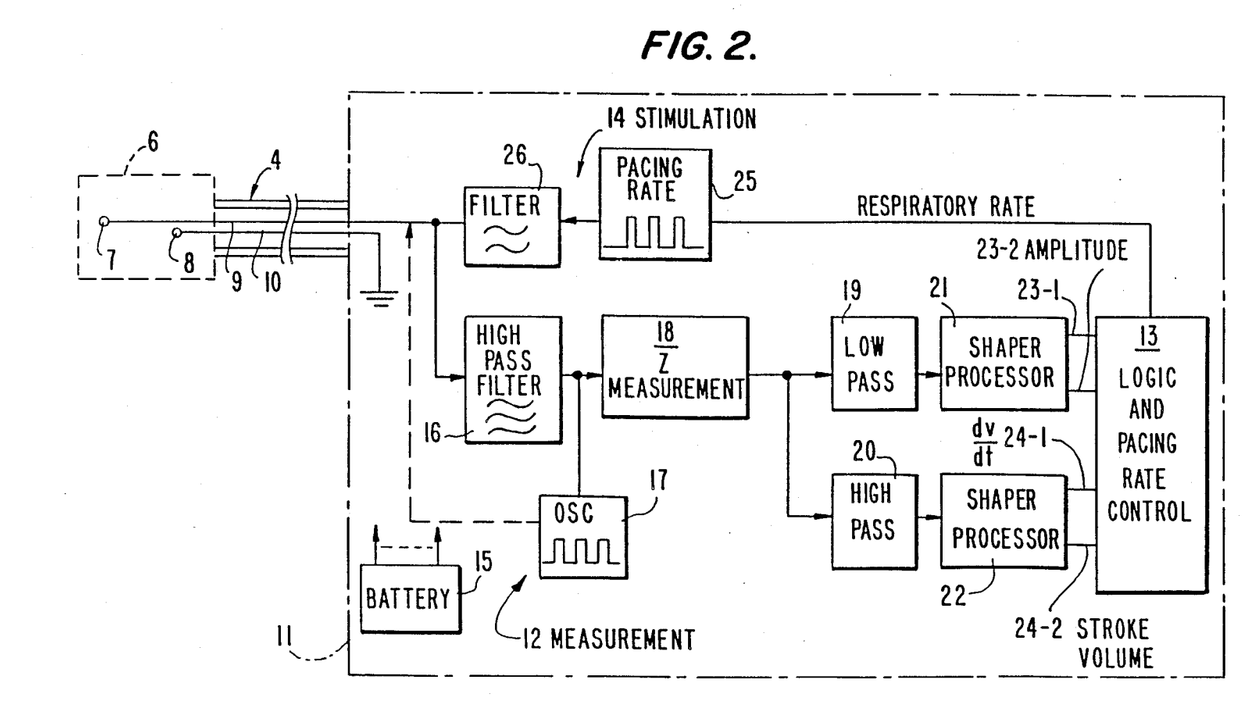

The block diagram control circuit 11 has functionally defined control circuit elements which can be embodied into an integrated circuit along with associated microprocessing means and appropriate software. The control circuit comprises generally a measurement section 12, a logic section 13 and a stimulation section 14. Energy is supplied by battery 15.

One line 10 from detector electrode pole 8 is connected to ground potential. The other detector signal line 9 is coupled to the signal measurement section 12 by high pass filter 16. An oscillator 17 provides alternating current for impedance measurement with a frequency between approximately 1 kHz and 100 kHz. This measurement signal is of such low comparative signal strength that it does not interfere with the stimulation of the heart at the commonly shared electrode 6. A low current amplitude in the range of a few microamperes, or alternatively single pulses of 0.01 msec duration and corresponding low amplitude, also reduces battery load. The current signal of oscillator 17 is shown applied to the measuring-stimulus electrode 6 by way of the dotted lead.

The resistance (or impedance) within the heart between the electrode 6 poles 7 and 8, as defined by Ohm's law, is determined in the impedance measuring means 18 following high-pass filter 16 which passes the signal at the oscillator 17 frequency, which is significantly higher than the pacing rate, which is thereby eliminated so that it can have no interfering effect on the impedance measurements. The resulting raw sensor signal varying dynamically in impedance is fed on one hand to a low-pass filter circuit 19 and on the other hand to a high-pass filter circuit 20, which splits the impedance modulated signal into lower and higher frequency portions. Thus, low-pass circuit 19 passes signals associated with the patient's lower respiratory rate, whereas high-pass circuit 20 passes signals associated with the patient's higher-rate cardiac activity. Since the heart rate is generally four to five times greater than the respiratory rate, these respiratory or pulmonary and cardiac signals can be separated with state of the art filters.

The output signals of low-pass and high-pass circuits 19, 20 are each fed to a respective signal shaping-processor circuits 21, 22 for preevaluation, e.g. averaging, amplitude and frequency analysis, determination of the derivative in time and subsequent integration, or the like. An output line 23-1 of low-pass circuit 21 then provides a signal associated with the respiratory rate and corresponding to the periodic frequency of the low-frequency signal. The further output line 23-2 provides a signal associated with the depth of respiration and corresponding to the amplitude of the low-frequency signal. An output line 24-1 of high-pass circuit 22 provides a signal associated with the contractility of the heart and corresponding to the derivative in time (dV/dt) of the high-pass filtered impedance signal, i.e. the rate of change in time of the systolic stroke volume (V). A further output line 24-2 provides a signal associated with the stroke volume of the heart and corresponding to the amplitude of the high-passed impedance signal.

All output lines 23, 24 are connected to logic and pacing rate control circuits 13, which includes a microprocessor to calculate on the basis of available signals, an optimum pacing rate related to the exercise of the pacemaker wearer. This pacing rate is fed to a pulse generator 25 in stimulation signal section 14, which provides corresponding stimulation pulses to the bipolar electrode 6 via a low pass filter 26 transmitting only the basic pacing pulses. The frequencies of measuring channel 12 and stimulation channel 14 are separated by filters 16 and 26 so that the signals in one channel do not interfere and impair the functioning of the other channel. In this manner the bi-polar electrode 6 can be used both as a measuring electrode and as a stimulation electrode.

Figure 3:
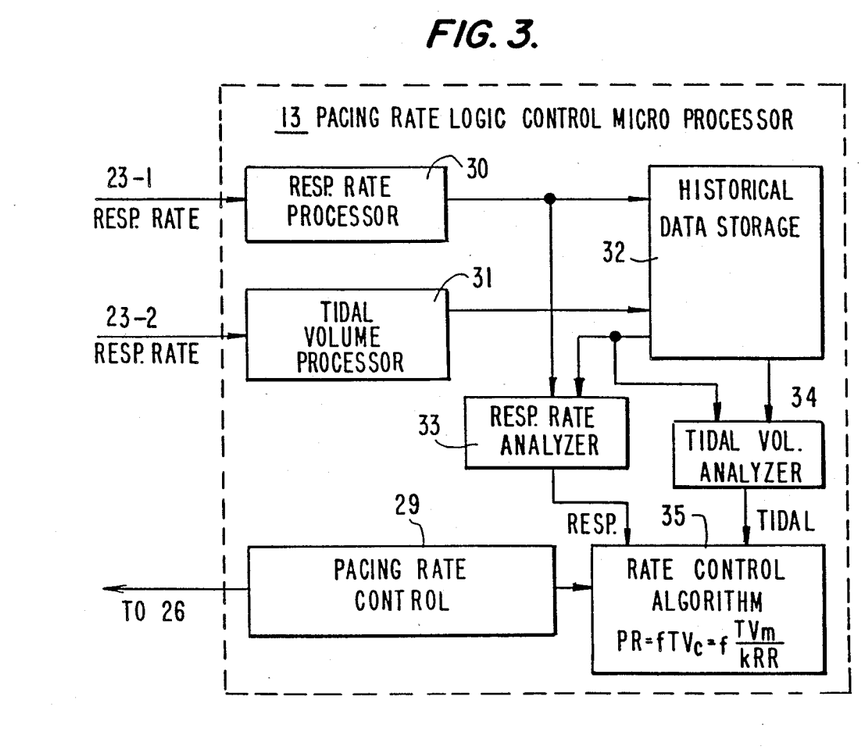

Further operation of the logic pacing rate control circuit 13, as afforded by this invention in connection with pulmonary activity analysis, is set forth in FIG. 3. Thus, the lower frequency pulmonary signals at 23-1 and 23-2 respectively relating to respiratory rate and respiratory signal amplitude are processed by respective circuits 30, 31, such as by digitizing to produce signals for use in the microprocessor contained in logic control section 13. Personal historical data pertinent to pacing rate is then stored at store 32 for making pacing control decisions based upon a patient's individual characteristics.

Analyzers and rate control processing systems 33, 34 and 35 then respectively process the respiratory rate and tidal volume current and historic signals to provide control signal data corresponding with a control algorithm determined for optimum pacing controls from those respective signals. In this respect each respiratory cycle is checked for amplitude and rate. The values are averaged over appropriate short term intervals, such as 20 seconds. Each amplitude value is then processed by a first correction function in order to compensate for distortion of the signals in the filters, if necessary, and then by a second correction function to correct the nonlinear pressure-volume relationship of the heart and individually different pulmonary compliance conditions, as later discussed. The microprocessor is thus programmed to make such comparisons and corrections to the rate control by suitable calculations with the amplitude and rate variables from the respiratory activity derived from the low pass filter 19 in FIG. 2.

Thus, respective control signals are then combined into a master control algorithm optimized for pacing rate control in block 35 for use by the pacing rate control circuit 25 that sends heart stimulation signals via filter 26 to the implanted stimulation electrode. In accordance with this invention one specific algorithmic relationship for control of the pacing rate is stated as $PR = f(TV_c) = f(TV_M/kRR)$, that is the pacing rate is a function of the corrected low pass amplitude representing tidal volume which is the measured instantaneous amplitude adjusted for nonlinearity as an inverse function of the respiratory rate.

The following waveform charts and general discussions will show how to provide appropriate programs to the microprocessor of control logic system 13 for producing control algorithms for optimal control of the pacing rate in accordance with policy selections made with appropriate medical advice. Accordingly such pacing systems as shown for example in Plicchi et al., No. 4,567,892, supra, Koning, et al., No. 4,566,456, Jan. 28, 1986, or Amundson, No. 4,722,342, supra may be modified to operate in accordance with the principles of this invention by those skilled in the cardiac pacer arts.

Figure 4A:
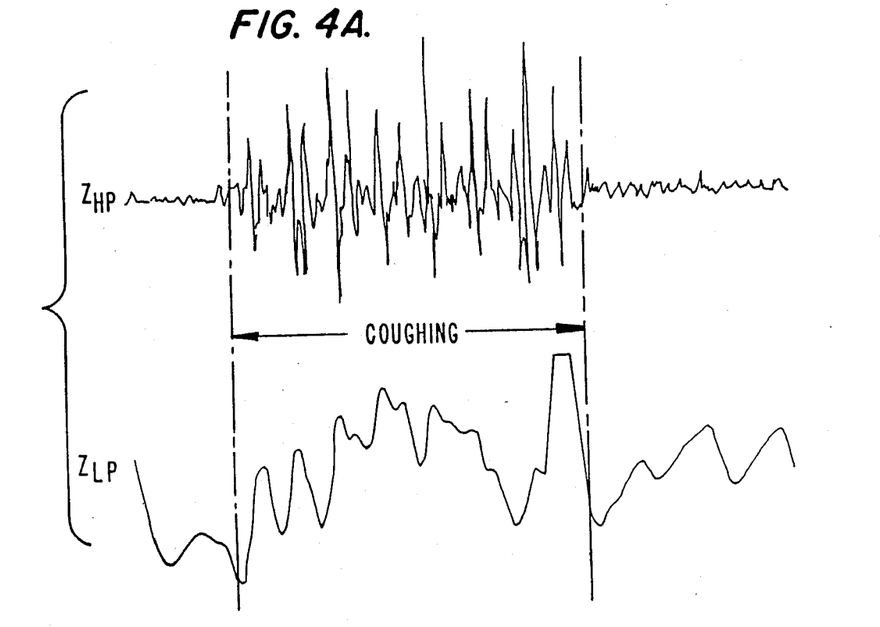
Figure 4B:
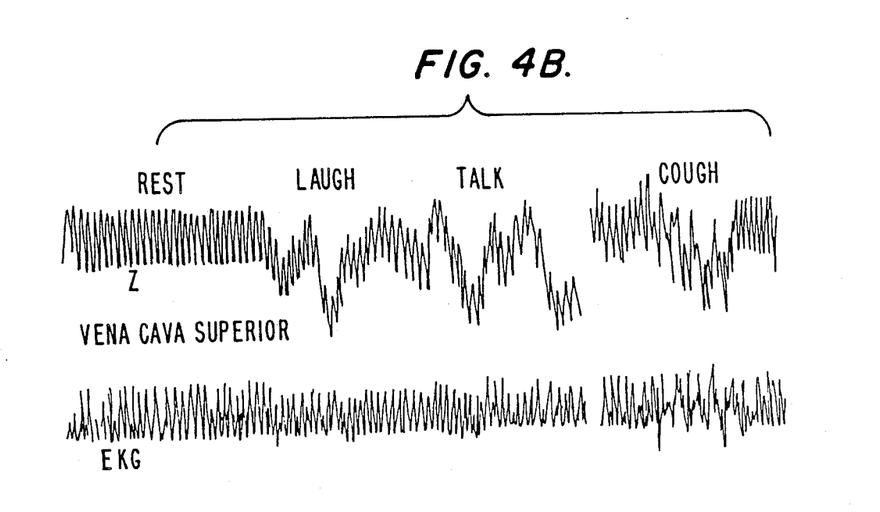
Figure 5A:
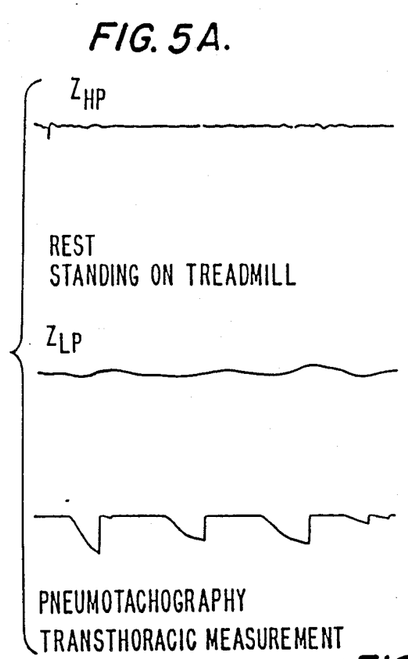
Figure 5B:
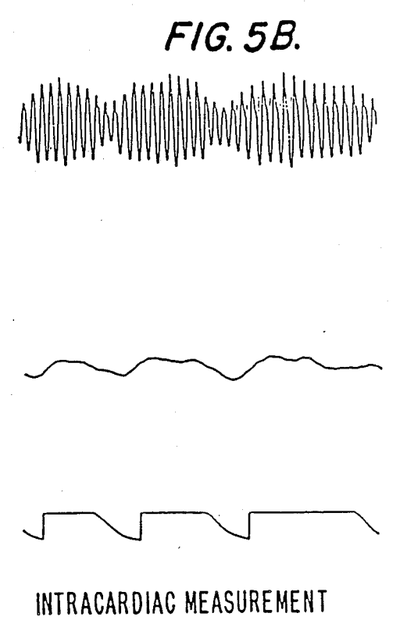

Further important aspects of the invention become evident from FIGS. 4 and 5, indicating that extraneous noise would dominate pacing rate control, thereby making unacceptable the control of pacing rates based upon vena cava superior or transthoracic measurements of the prior art. Thus, in FIG. 4A, the effect of coughing in such signals becomes prominent. It is clear that coughs should not control the pacing rate. FIG. 4B further makes clear that laughing and talking would control the pacing rate if these prior art impedance measurements were used for pacing rate controls.

The comparison of the transthoracic measurements suggested by the prior art with the intracardiac measurements of the present invention is made in FIG. 5. Here three signals are compared, namely the signals from a high pass filter $Z_{HP}$, the signals from a low pass filter $Z_{LP}$ and actual pheumotachography breathing signals representative of respiratory rates and tidal volumes (shown by amplitude). In the high pass signals, the intracardiac measurement method provides heartbeat signals at a frequency higher than the respiratory rate, which do not occur in transthoracic measurements excluding the catheter tip.

The significantly improved low pass signals containing the respiratory information show a good correlation between the the directory measured ventilation and those ventilatory signals taken by the intracardiac sensing according to this invention.

Our investigations therefore are aimed in a completely new direction of measuring the pulmonary changes due to breathing, not directly in the thoracic cavity as proposed up to now, and thereby registering the increase of impedance due to inhalation, but detecting indirectly the influence of intrathoracic pressure fluctuations correlated with breathing on the change of intracardiac impedance.

The theoretical basis of this invention is based on the fact that when the intrathoracic pressure drops during inhalation the volume of the lung increases. An approximately linear relation between the change in intrathoracic pressure and the change in lung (tidal) volume is given both in healthy persons and in elderly patients for a significant range of normal pulmonary activity, as shown in FIG. 7B. However personal adjustments may be desirable for different individual patients, which might have a more or less steep slope of this relationship. The change in intrathoracic pressure is in turn propagated directly to the heart. These pressure fluctuations lead to variations of intracardiac pressure. When no restrictive pericardial disease is present, these fluctuation are transmitted unchanged to the heart by the pericardium surrounding the heart. The intracardiac pressure fluctuations in turn result in a shift of volume within the heart, which in accordance with this invention is measured as impedance changes at the pacing electrode.

Considering the impedance signal provided by this invention for the respiratory action, the inhalation phase is associated with a drop of pressure in the esophagus as a representative value of intrathoracic pressure, and the exhalation phase with a pressure increase. Pressure transmission to the heart causes, due to inhalation, the corresponding greater abundance of blood in the heart and thus an inspiratorily smaller impedance.

Figure 6:
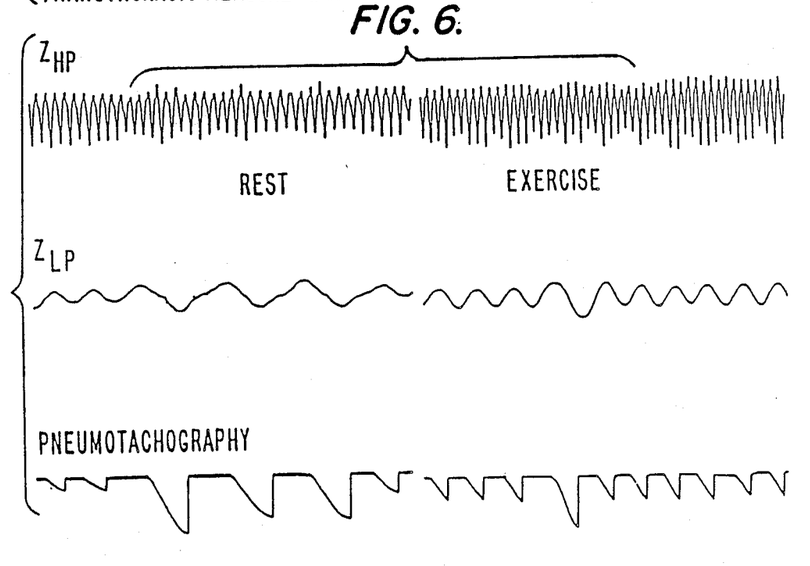
FIG. 6 is a signal waveform chart showing the historic comparisons of ventilation parameters at rest and during exercise, and the corresponding high and low pass impedance signals measured according to the invention within the heart, and FIGS. 7A and B are simplified charts showing respectively the pressure-volume relationships of different patients in the right heart and the intrathoracic pressure-tidal volume characteristic.

The waveforms of FIG. 6 will demonstrate the need for developing the aforesaid pacer control rate algorithm taking into account the nonlinearity of the tidal wave amplitude readings from intracardiac impedace measurement as a function of the respiration rate. This takes into account the non-linear pressure-volume relation of the heart. Further correction can be made for the individually different pulmonary compliance as set forth in FIG. 7A.

Thus, in FIG. 6 the measured low frequency respiratory signals $Z_{LP}$ and the high frequency cardiac signals $Z_{HP}$ are shown for rest and exercise, and compared with the actual breathing signal (Pneumotachography). It should be clear from these signals that the measured low pass filtered amplitude of the impedance signal that represents tidal volume can not be used uncorrected to control pacing rates, because the heart pressure-volume response is nonlinear, as will be seen later from FIG. 7A. Corrections accordingly have to be made by the pacing rate master control algorithm from stored historic signals and logic decisions made from comparison of the tidal volume signal and the respiratory rate signals available from the measurements as shown in FIG. 2.

Thus it is seen from FIG. 6 that at several respiratory rates the amplitude of the low pass filtered impedance signal at rest and during exercise is substantially the same. However, the corresponding directly measured (by pneumotachography) true tidal volume differs almost by a factor of two. Also it is clear that the respiration rate is lower at rest than during exercise. This demonstrates applicant's finding that for proper pulse rate control as a function of the tidal volume taken from intracardiac impedance measurements therefore correction of the raw measured impedance tidal volume signal is needed. It was found as demonstrated here that the measured impedance amplitude representing tidal volume decreases from the true tidal volume as a function of increasing ventricular filling pressures with increasing exercise. Since the measurement of filling pressure in impedance controlled pacemakers is not available, according to the present invention it is found that the respiratory rate correlates positively to filling pressure. Therefore in the pacemaker control algorithm the respiratory rate, which is known, replaces filling pressure in that pressure-volume relation depicted in FIG. 7A. The decrease in volume (delta $V_1$ to delta $V_2$) is therefore corrected by a factor that is a function of repiratory rate. That means, the higher the respiratory rate, the more the amplitude of the measured tidal volume is suppressed, making the tidal volume amplitude correction factor an inverse function of the respiration rate. This then can be generally expressed in algorithmic form as $PR = f(TV_M/kRR)$, namely that the pacing rate is a function of the measured tidal volume inversely adjusted in proportion to the respiratory rate. This algorithmic relationship thus can be programmed into the performance of the microprocessor logic of the pacemaker set forth in FIGS. 2 and 3.

Further control decisions need be made in deriving optimum pacing rate control signals from sensed respiratory activity. One primary influencing factor is the physical condition of the particular individual patient. Another significant factor is the non-linearity relationship of the true tidal volume signals to the amplitudes of the measured impedance signals.

Figure 7A:
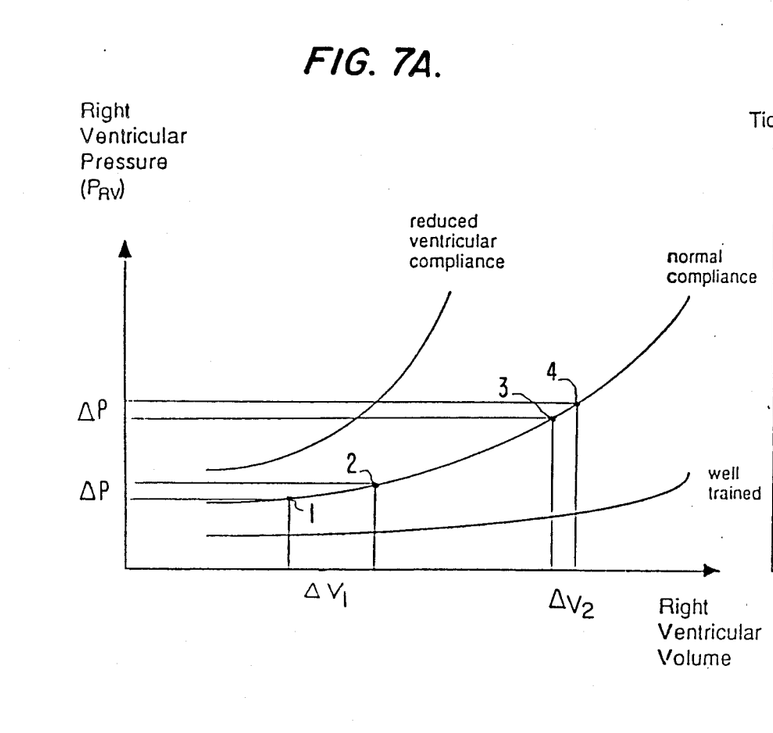
Figure 7B:
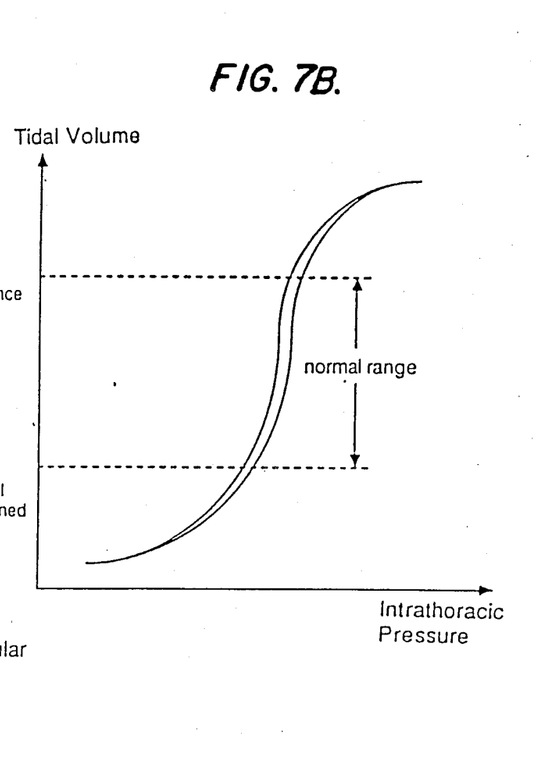

The nonlinear response of the heart to the volume-pressure relationship is also evidenced by FIG. 7A. If the normal compliance curve is considered, it is seen that the same change of pressure exhibits a different change of volume at the lower and higher portions of the curve.

Now consider the theoretic basis for more accurate pacing rate controls as afforded by this invention with reference to the charts of FIG. 7. With ventilation in the normal range, a nearly linear relation between changes in intrathoracic pressure and effected ventilation (tidal volume) exists. The slope of this relation expresses the individual pulmonary compliance and describes the intrathoracic pressure changes that are needed to efect a certain tidal volume. The intrathoracic pressure changes are transmitted to the heart and effect changes in right ventricular pressure. Those changes result in variations of right ventricular volume. The relation of intracardiac pressure to volume changes depends not only on the general state of the myocardium (ventricular compliance) but also on the current position on the myocardial pressure-volume characteristic line.

A patient is at rest and his ventricular pressure and volume correspond to point 1 on the normal compliance curve. A respiration induced change in right ventricular pressure of dP induces a movement on the compliance curve to point 2 resulting in a rather large change of right ventricular volume $dV_1$. When the same patient is at a different hemodynamic state, for example with physical exercise, and his ventricular volume and pressure have increased to point 3 on the compliance curve, the same change dP in right ventricular pressure from the same true tidal volume will however only move to point 4 inducing a much smaller $dV_2$ change of volume in the heart.

Therefore the amplitudes of intracardiac impedance thus used as an indirect measure of tidal volume have to be corrected by the function of the respective compliance for the particular patient. Since this function also correlates with respiratory rate (with exercise, respiratory rate, ventricular volume and right ventricular pressure increase), for the purpose of simplicity, the correction factor for compliance is adjusted according to the current respiratory rate. Thus, depending upon the specific pacemaker system construction a proportionality is established between respiratory rate and tidal volume. The logic control system 13 of FIG. 2 thus establishes a pacing rate control that adjusts the measured tidal volume amplitude at 23-2 to a true value as a function of the respiratory rate at 23-1. In a microprocessor controlled pacemaker, more complex correctional algorithms may be used. In any event the proportionality ratio should be adjustable for different compliances to tailor fit the pacing rate to individual patients.

It is evident therefore that this invention provides novel and improved sensing and pacing control means and methods including specifically improved ventilation control of rate responsive cardiac pacemakers. Thus, tailored control of pacing rates to meet the personal attributes and needs of the patient in a simplified installation with a choice of control algorithms now is made feasible. Having therefore advanced the state of the art, those features of novelty typical of the spirit and nature of the invention are defined with particularity in the following claims.

I claim:

1. Heart measurement instrumentation comprising in combination,
   measurement means for producing a measurement signal responsive to intracardiac pressure and volume of a patient,
   processing means for the measurement signal including means for isolating from the measurement signal separate ventilatory function signals displaying variable amplitude and respiratory rate related to respiratory activity of a patient, and
   tidal volume detection means for processing the amplitude of the ventilatory function signals as a function of the respiratory rate to produce a corrected amplitude reflecting the true ventilatory tidal volume of the patient over a wide range of patient activity.

2. Instrumentation as defined in claim 1 further comprising:
   pulse generator means for generating heart pacing pulses,
   electrode means adapted to be located in the right heart for receiving the pacing pulses, and
   pacer rate control means for controllably changing the rate of the heart pacing pulses in response to said corrected amplitude reflecting true ventilatory tidal volume.

3. Instrumentation as defined in claim 2, wherein said measuring means further comprises:
   impedance measuring means responsive to intracardial impedance detected by said electrode means.

4. Instrumentation as defined in claim 3 further comprising:
   common conveyance means for transmitting the pacing signals to the electrode means and receiving the measurement signals from the electrode means, and
   means for preventing interference between measurement signals and pacing signals comprising means for inducing impedance measurements with periodic electric signals conveyed to the electrode of low enough energy that they are unable to pace the heart.

5. Instrumentation as defined in claim 4 further comprising:
   low pass filter means for processing the measurement signals for isolating said ventilatory function signals from the measurement signals.

6. The instrumentation defined in claim 1 wherein said measurement means further comprises:
   electrode means adapted to be implanted in a patient's body for continually monitoring and analyzing intracardiac activity to produce said measurement signal and means responsive to a measurement signal component isolated by means of a low frequency filter representative of respiratory physiological variables for producing pacing pulses at said electrode means.

7. The method of controlling heart pacing rate of a patient in pacemaker systems, comprising the steps of:
   implanting an electrode in the patient's right heart,
   providing periodic hear pacing pulses to the electrode,
   sensing cardiac activity by monitoring intracardiac parameters presented to said electrode,
   deriving from said cardiac activity a set of ventilatory signals representative of variable respiratory activity of the patient,
   processing the ventilatory signals so as to derive subsignals representing respiratory rate and tidal volume,
   modifying the tidal volume subsignal as a function of the respiratory rate subsignal so as to derive a pulse rate control algorithm, and
   controlling the pacing rate as a function of said control algorithm.

8. The method of producing heart pacing rate signals comprising the steps of:
   deriving signals responsive to exercise of a patient from intracardiac measurements reflecting volume and pressure,
   separating from said intracardiac measurements separate ventilatory signals relating to a patient's tidal volume and respiratory rate, and
   deriving a corrected tidal volume signal reflecting the effect of exercise of the patient as a selected function of said signals from the intracardiac measurements.

9. The method of claim 8 wherein the selected function of intracardiac measurements is a respiratory rate signal derived from said signals from the intracardiac measurements.

10. The method of claim 8 further wherein the step of deriving signals responsive to exercise of a patient further comprises sensing cardiac activity from a single electrode consisting of a pacing electrode adapted to be implanted in a patient to receive said pacing rate signals.

11. The method of claim 10 further wherein the step of deriving signals responsive to exercise of a patient further comprises measurement of impedance in the right side of the heart.

12. Instrumentation as defined in claim 1 wherein said measurement means comprises a single detection electrode consisting of a pacing electrode adapted to be located in the right side of the heart for receiving pacing pulses.

* * * * *